(12) United States Patent
Prandi et al.

(10) Patent No.: US 8,556,946 B2
(45) Date of Patent: Oct. 15, 2013

(54) ORTHOPEDIC IMPLANT IN THE FORM OF A PLATE TO BE FIXED BETWEEN TWO BONE PARTS

(75) Inventors: Bernard Prandi, Rennes (FR); Keith Wapner, Philadelphia, PA (US); Charles P. Wapner, Media, PA (US); Peter W. Wapner, Media, PA (US)

(73) Assignee: Memometal Technologies (FR)

( * ) Notice: Subject to any disclaimer, the term of this patent is extended or adjusted under 35 U.S.C. 154(b) by 420 days.

(21) Appl. No.: 12/918,071

(22) PCT Filed: Oct. 2, 2009

(86) PCT No.: PCT/FR2009/051879
§ 371 (c)(1),
(2), (4) Date: Oct. 29, 2010

(87) PCT Pub. No.: WO2010/037985
PCT Pub. Date: Apr. 8, 2010

(65) Prior Publication Data
US 2011/0046681 A1    Feb. 24, 2011

(30) Foreign Application Priority Data

Oct. 2, 2008   (FR) ...................................... 08 56694

(51) Int. Cl.
*A61B 17/80*   (2006.01)

(52) U.S. Cl.
USPC ........................................................ 606/286

(58) Field of Classification Search
USPC ................ 606/60, 70, 71, 280–299, 246–279
See application file for complete search history.

(56) References Cited

U.S. PATENT DOCUMENTS

| | | | |
|---|---|---|---|
| 2,486,303 A | 10/1949 | Longfellow | |
| 3,528,085 A | 9/1970 | Reynolds | |
| 3,534,731 A | 10/1970 | Muller | |
| 3,552,389 A | 1/1971 | Allgower et al. | |
| 3,779,240 A | 12/1973 | Kondo | |

(Continued)

FOREIGN PATENT DOCUMENTS

| | | |
|---|---|---|
| DE | 3027148 A1 | 12/1981 |
| DE | 8227727 U | 1/1983 |

(Continued)

OTHER PUBLICATIONS

Manual of Small Animal Fracture Repair and Management, Jan. 1, 1998, pp. 80-81.

(Continued)

*Primary Examiner* — Kevin T Truong
*Assistant Examiner* — Christopher Beccia
(74) *Attorney, Agent, or Firm* — Lerner, David, Littenberg, Krumholz & Mentlik, LLP

(57) ABSTRACT

The invention relates to a plate fixed between two bone parts by way of screws engaged in holes formed in the thickness of the plate. The plate comprises an angled member or rib which is inclined according to an angle of between about 30° and 60° in relation to the plane defined by the plate. The angled member or rib has a hole for engaging a screw and is located in the central part of the width, over a determined part of the length of the plate, so that the screw brings the two bone parts into a compressive position.

39 Claims, 2 Drawing Sheets

(56) References Cited

U.S. PATENT DOCUMENTS

Figure 1:
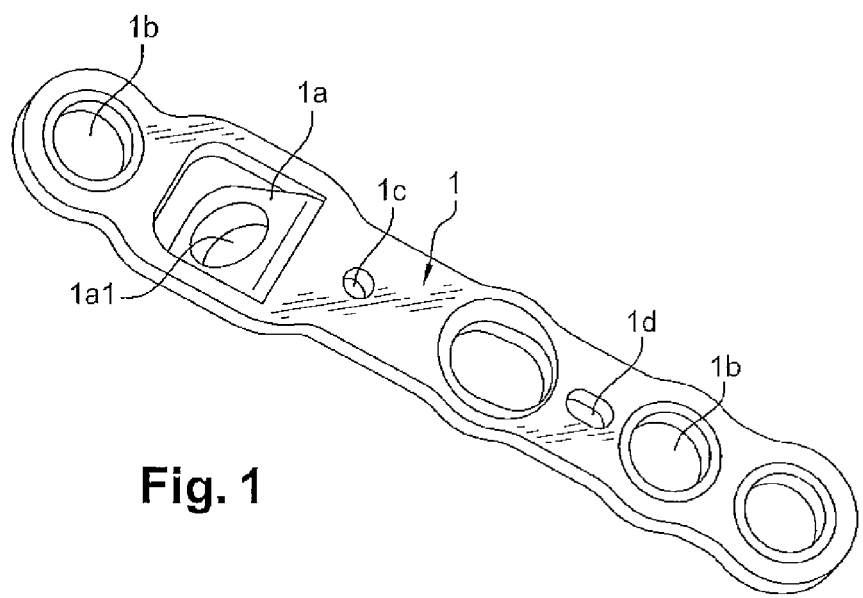

| | | | |
|---|---|---|---|
| RE2,884 E | 6/1976 | Allgower et al. |
| 4,388,921 A | 6/1983 | Sutter et al. |
| 4,408,601 A | 10/1983 | Wenk |
| RE31,628 E | 7/1984 | Allgower et al. |
| 4,493,317 A | 1/1985 | Klaue |
| 4,503,737 A | 3/1985 | DiGiovanni |
| 4,513,744 A | 4/1985 | Klaue |
| 4,651,724 A | 3/1987 | Berentey et al. |
| 4,800,874 A | 1/1989 | David et al. |
| 4,957,496 A | 9/1990 | Schmidt |
| 4,988,350 A | 1/1991 | Herzberg |
| 5,105,690 A | 4/1992 | Lazzara et al. |
| 5,304,180 A | 4/1994 | Slocum |
| 5,347,894 A | 9/1994 | Fischer |
| 5,487,741 A | 1/1996 | Maruyama et al. |
| 5,662,655 A | 9/1997 | Laboureau et al. |
| 5,667,510 A | 9/1997 | Combs |
| 5,674,222 A | 10/1997 | Berger et al. |
| 5,709,686 A | 1/1998 | Talos et al. |
| 5,810,822 A | 9/1998 | Mortier |
| 5,827,285 A | 10/1998 | Bramlet |
| 5,853,413 A | 12/1998 | Carter et al. |
| 5,904,684 A | 5/1999 | Rooks |
| 5,931,839 A | 8/1999 | Medoff |
| 6,146,382 A | 11/2000 | Hurlbert |
| 6,183,475 B1 | 2/2001 | Lester et al. |
| 6,348,052 B1 | 2/2002 | Sammarco |
| 6,379,359 B1 | 4/2002 | Dahners |
| 6,383,186 B1 | 5/2002 | Michelson |
| 6,533,786 B1 | 3/2003 | Needham et al. |
| 6,544,266 B1 | 4/2003 | Roger et al. |
| 6,565,570 B2 | 5/2003 | Sterett et al. |
| 6,576,018 B1 | 6/2003 | Holt |
| 6,623,486 B1 | 9/2003 | Weaver et al. |
| 6,626,907 B2 | 9/2003 | Campbell et al. |
| 6,669,700 B1 | 12/2003 | Farris et al. |
| 6,669,701 B2 | 12/2003 | Steiner et al. |
| 6,692,503 B2 | 2/2004 | Foley et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,960,211 B1 | 11/2005 | Pfefferle et al. |
| 7,037,342 B2 | 5/2006 | Nilsson et al. |
| 7,108,697 B2 | 9/2006 | Mingozzi et al. |
| 7,137,987 B2 | 11/2006 | Patterson et al. |
| 7,179,260 B2 * | 2/2007 | Gerlach et al. ............... 606/291 |
| 7,326,218 B2 | 2/2008 | Sterett et al. |
| 7,341,589 B2 | 3/2008 | Weaver et al. |
| 7,344,538 B2 | 3/2008 | Myerson et al. |
| D587,370 S | 2/2009 | Coillard-Lavirotte et al. |
| 7,491,220 B2 | 2/2009 | Coughln |
| D596,294 S | 7/2009 | Coillard-Lavirotte et al. |
| 7,695,472 B2 | 4/2010 | Young |
| 7,766,948 B1 | 8/2010 | Leung |
| 7,771,457 B2 | 8/2010 | Kay et al. |
| D623,745 S | 9/2010 | Kay et al. |
| 7,799,061 B2 | 9/2010 | Kay et al. |
| 7,819,903 B2 | 10/2010 | Fraser et al. |
| 7,857,836 B2 | 12/2010 | Huebner et al. |
| 7,931,680 B2 | 4/2011 | Myerson et al. |
| 8,080,010 B2 | 12/2011 | Schulz et al. |
| 8,100,954 B2 | 1/2012 | Kay et al. |
| 8,100,983 B2 | 1/2012 | Schulte |
| 2001/0011172 A1 | 8/2001 | Orbay et al. |
| 2001/0047172 A1 | 11/2001 | Foley et al. |
| 2002/0045901 A1 | 4/2002 | Wagner et al. |
| 2002/0183752 A1 | 12/2002 | Steiner et al. |
| 2003/0060827 A1 | 3/2003 | Coughlin |
| 2003/0195516 A1 | 10/2003 | Sterett et al. |
| 2003/0199875 A1 | 10/2003 | Mingozzi et al. |
| 2004/0059334 A1 | 3/2004 | Weaver et al. |
| 2004/0092929 A1 | 5/2004 | Zindrick |
| 2004/0093081 A1 | 5/2004 | Nilsson et al. |
| 2004/0167522 A1 | 8/2004 | Niederberger et al. |
| 2004/0172028 A1 | 9/2004 | Roger |
| 2004/0181228 A1 | 9/2004 | Wagner et al. |
| 2004/0186477 A1 | 9/2004 | Winquist et al. |
| 2004/0210234 A1 | 10/2004 | Coillard-Lavirotte et al. |
| 2004/0214137 A1 | 10/2004 | Walton |
| 2004/0236332 A1 | 11/2004 | Frigg |
| 2005/0015089 A1 | 1/2005 | Young et al. |
| 2005/0070904 A1 | 3/2005 | Gerlach et al. |
| 2005/0080421 A1 | 4/2005 | Weaver et al. |
| 2005/0085913 A1 | 4/2005 | Fraser et al. |
| 2005/0090825 A1 | 4/2005 | Pfefferle et al. |
| 2005/0171544 A1 | 8/2005 | Falkner |
| 2005/0182408 A1 | 8/2005 | Pfefferle et al. |
| 2005/0277937 A1 | 12/2005 | Leung et al. |
| 2006/0004362 A1 | 1/2006 | Patterson et al. |
| 2006/0015102 A1 | 1/2006 | Toullec et al. |
| 2006/0058796 A1 | 3/2006 | Hartdegen et al. |
| 2006/0106387 A1 | 5/2006 | Fanger et al. |
| 2006/0149261 A1 | 7/2006 | Nilsson et al. |
| 2006/0173459 A1 | 8/2006 | Kay et al. |
| 2006/0200145 A1 | 9/2006 | Kay et al. |
| 2006/0235397 A1 | 10/2006 | Sanders et al. |
| 2006/0241607 A1 | 10/2006 | Myerson et al. |
| 2006/0241608 A1 | 10/2006 | Myerson et al. |
| 2006/0241609 A1 | 10/2006 | Myerson et al. |
| 2007/0142920 A1 | 6/2007 | Niemi |
| 2007/0233106 A1 | 10/2007 | Horan et al. |
| 2007/0270850 A1 | 11/2007 | Geissler |
| 2008/0015593 A1 | 1/2008 | Pfefferle et al. |
| 2008/0051791 A1 | 2/2008 | Young et al. |
| 2008/0091197 A1 | 4/2008 | Coughlin |
| 2008/0114360 A1 | 5/2008 | DaFrota Carrera |
| 2008/0132960 A1 | 6/2008 | Weaver et al. |
| 2008/0161860 A1 | 7/2008 | Ahrens et al. |
| 2008/0208262 A1 | 8/2008 | Butler et al. |
| 2008/0249572 A1 | 10/2008 | Tandon |
| 2008/0249573 A1 | 10/2008 | Buhren et al. |
| 2009/0024173 A1 | 1/2009 | Reis, Jr. |
| 2009/0036933 A1 | 2/2009 | Dube et al. |
| 2009/0093849 A1 | 4/2009 | Grabowski |
| 2009/0118769 A1 * | 5/2009 | Sixto et al. ............... 606/280 |
| 2009/0198285 A1 | 8/2009 | Raven, III |
| 2009/0210010 A1 | 8/2009 | Strnad et al. |
| 2009/0210011 A1 | 8/2009 | Den Hartog et al. |
| 2009/0210013 A1 | 8/2009 | Kay et al. |
| 2009/0228048 A1 | 9/2009 | Duncan et al. |
| 2009/0234359 A1 | 9/2009 | Onoue et al. |
| 2009/0275987 A1 | 11/2009 | Graham et al. |
| 2009/0306724 A1 | 12/2009 | Leither et al. |
| 2009/0312759 A1 | 12/2009 | Ducharme et al. |
| 2010/0016900 A1 | 1/2010 | Terres et al. |
| 2010/0057214 A1 | 3/2010 | Graham et al. |
| 2010/0121324 A1 | 5/2010 | Tyber et al. |
| 2010/0121325 A1 | 5/2010 | Tyber et al. |
| 2010/0125300 A1 | 5/2010 | Blitz et al. |
| 2010/0160973 A1 | 6/2010 | Leung |
| 2010/0217328 A1 | 8/2010 | Terrill et al. |
| 2010/0256638 A1 | 10/2010 | Tyber et al. |
| 2010/0256639 A1 | 10/2010 | Tyber et al. |
| 2010/0274293 A1 | 10/2010 | Terrill et al. |
| 2010/0305618 A1 | 12/2010 | Kay et al. |
| 2010/0324556 A1 | 12/2010 | Tyber et al. |
| 2011/0004253 A1 | 1/2011 | Fraser et al. |
| 2011/0009866 A1 | 1/2011 | Johnson et al. |
| 2011/0087229 A1 | 4/2011 | Kubiak et al. |
| 2011/0087295 A1 | 4/2011 | Kubiak et al. |
| 2011/0092981 A1 | 4/2011 | Ng et al. |
| 2011/0093017 A1 | 4/2011 | Prasad et al. |
| 2011/0093018 A1 | 4/2011 | Prasad et al. |
| 2011/0118739 A1 | 5/2011 | Tyber et al. |
| 2011/0125153 A1 | 5/2011 | Tyber et al. |
| 2011/0213367 A1 | 9/2011 | Tyber et al. |
| 2011/0218535 A1 | 9/2011 | Wang et al. |
| 2011/0230884 A1 | 9/2011 | Mantzaris et al. |
| 2011/0264148 A1 | 10/2011 | Prandi et al. |

(56) References Cited

U.S. PATENT DOCUMENTS

2011/0306976 A1  12/2011  Kubiak et al.
2011/0306977 A1  12/2011  Michel et al.

FOREIGN PATENT DOCUMENTS

| | | | |
|---|---|---|---|
| DE | 3630862 A | | 3/1988 |
| EP | 0 705 572 A2 | | 4/1996 |
| EP | 1707227 A2 | | 10/2006 |
| EP | 1897509 A1 | | 3/2008 |
| FR | 590290 B | | 3/1925 |
| FR | 590290 A | | 6/1925 |
| FR | 2362616 A1 | | 3/1978 |
| FR | 2764183 A1 | | 12/1998 |
| FR | 2846870 A1 | | 5/2004 |
| FR | 2912895 A1 | | 8/2008 |
| WO | 9516403 A1 | | 6/1995 |
| WO | 9528887 A1 | | 11/1995 |
| WO | 02098306 A1 | | 12/2002 |
| WO | 2007131287 A1 | | 11/2007 |

OTHER PUBLICATIONS

Catalogue General 1987-1988, plaques d'osteosynthese, bone plates, Division of Pfzer Hospital Products Group, Bagneux, France.

* cited by examiner

ORTHOPEDIC IMPLANT IN THE FORM OF A PLATE TO BE FIXED BETWEEN TWO BONE PARTS

CROSS REFERENCE TO RELATED APPLICATIONS

This application is the US national phase of PCT application PCT/FR2009/051879, filed 2 Oct. 2009, published 8 Apr. 2010 as 2010/037985, and claiming the priority of French patent application 0856694 itself filed 2 Oct. 2008, whose entire disclosures are herewith incorporated by reference.

The invention relates to the technical field of orthopedic implants.

More particularly, the invention relates to a plate for arthrodesis or osteosynthesis adapted to be fixed between two bone parts.

In a manner known to one having ordinary skill in the art, this type of plate generally has holes for engaging screws, allowing arthrodesis between two bones or osteosynthesis between two bone fragments. This is, for example, the case for bones of the hand or foot, without however excluding other applications, particularly in the field of the spine. Depending on the pathology to be treated, these plates can have a general rectilinear or other geometric shapes.

From this state of the art, one of the objects the invention proposes to attain is to improve, in a sure and efficient manner, compression in a precise direction between the bone parts subjected to the plate.

To attain the given object to enhance the compression between the two relative bone parts, according to the invention, the plate has a formation that orients at least one screw at an angle with respect to a plane defined by the plate, the angle being between about 30° and 60°.

According to an advantageous embodiment, the formation is a tab that is angled according to an angle between 30° and 60°, and having a hole for engaging the screw. The angled tab results from a cut out and a deformation of a portion of the plate.

In another embodiment, the formation is a hole angled at an angle between 30° and 60° for engaging the screw.

Considering the problem to be solved, the formation is located on a determined portion of the length of the plate so that the screw ensures the compression of the two bone parts.

Figure 2:
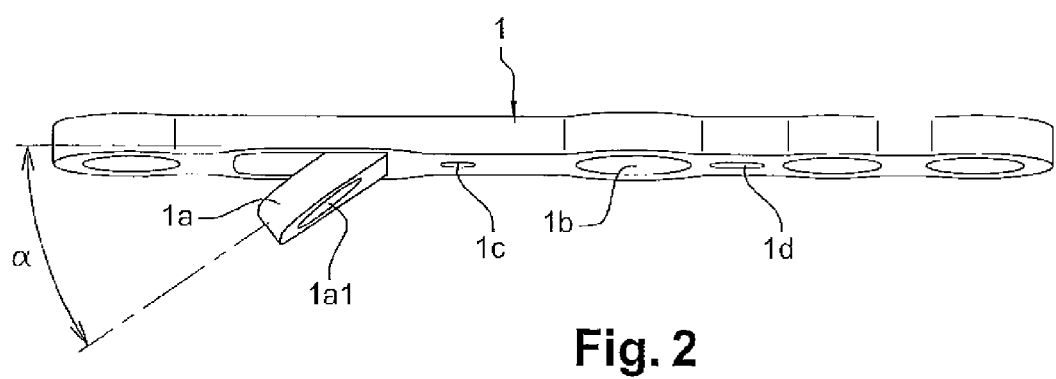
Figure 3:
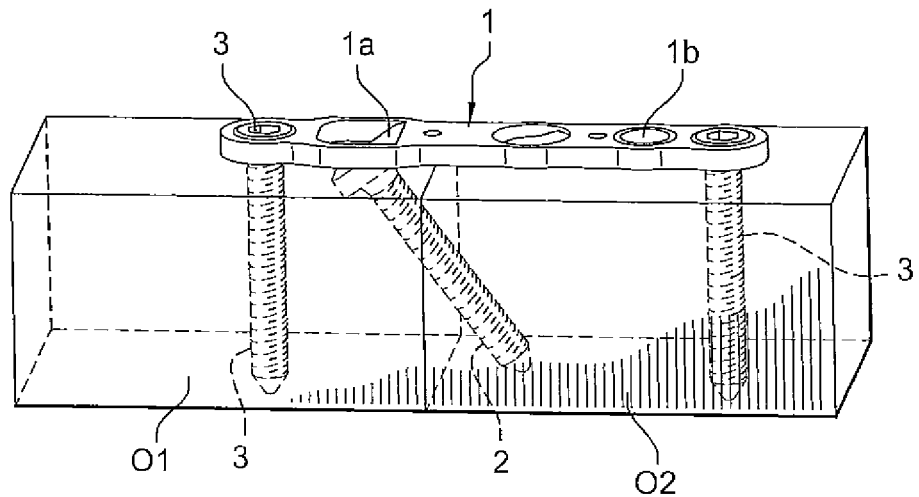
Figure 4:
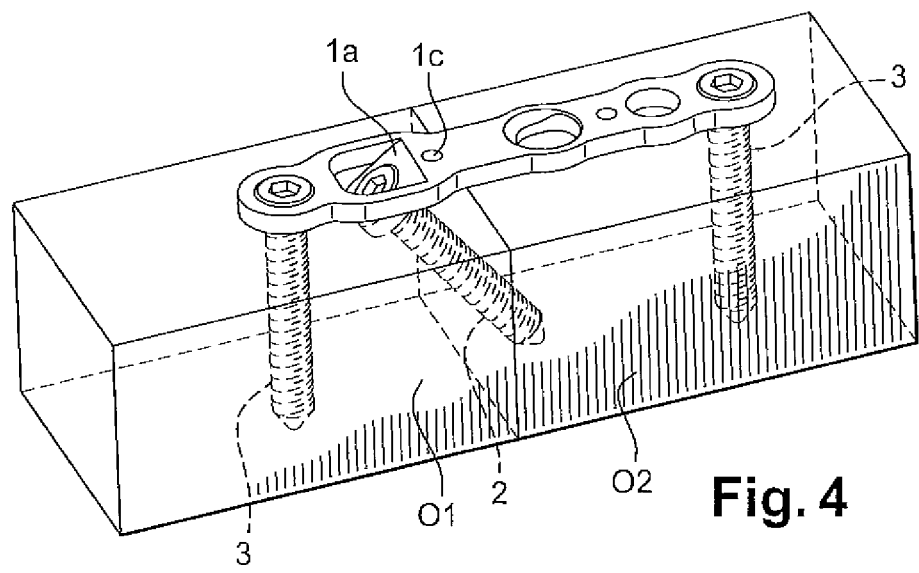

The invention is described hereinafter in more detail, with reference to the attached drawing in which:

FIG. 1 is a perspective view of an embodiment of the plate;
FIG. 2 is a side view of the plate;
FIGS. 3 and 4 are perspective views showing the mounting of the plate between two bone parts and their orientation by means of the plate according to the invention, the bone parts being shown schematically.

According to the invention, the plate 1 has at least one formation 1a adapted to enable the positioning of at least one screw 2, at an angle α of between 30° and 60° with respect to a plane of the plate (FIG. 2).

In one embodiment, the formation 1a is an angled tab cut out and deformed from the plate. For example, the deformation is made with a cutting-punching operation. This angled tab has a hole 1a1 for a screw 2. The angled tab 1a is positioned along the length of the plate so that after the screw 2 is fitted to it, the screw ensures the compression together of the two bone parts, as indicated below in the description.

In another embodiment, to allow for an angular orientation of the screw 2 according to an angle between about 30° and 60°, the formation 1a can be formed as an angled hole. It must be noted that the tab 1a enables adaptation of the angle as a function of the pathology to be treated, given that it is possible to deform this tab at will. In other words, the angle can be adjusted over a few degrees by the surgeon in the operating room, using an appropriate tool.

With reference to FIGS. 3 and 4 that show the positioning of the plate 1 between two bone parts O1 and O2:

Once the osteotomies have been carried out, a template of the plate, which does not have a guide formation, enables the position of this tab to be determined.

After determining the position of the tab, the surgeon makes a corresponding recess with the appropriate rasp.

Once the plate having the tab has been positioned, the surgeon sets one or two screws 3, on a side of the site of the osteosynthesis of the arthrodesis toward the tab. A temporary fastening pin can, possibly, be positioned in an complementary lug.

The screw 2 is then engaged in the hole 1a1 of the tab 1a to place the fracture in compression.

Once the compression has been done, the surgeon can screw one or several other additional fastening screws 3 and remove the temporary pin.

In a known manner, this plate 1 has smooth and/or threaded holes for the fastening screws 3 set in the bone parts O1 and O2 to engage in, as shown in FIGS. 3 and 4.

Similarly, the plate 1 can have at least one hole 1c for a pin for temporarily positioning the plate 1. Advantageously, the plate 1 can have a guide 1c for the insertion of a pin on the side of one of the bone parts O1 and another guide 1d for the insertion of another pin on the side of the other bone part O2.

Considering the effect of the desired compression, such as indicated above, the guide 1c is a circular hole whose diameter corresponds substantially to that of the pin 4, whereas the other guide 1d can be an elongated slot.

These provisions thus enable the bone to slide under the plate 1 as the screws are set, while ensuring compression along a precise direction, generally axially or parallel to the plate. The pins are of any known and appropriate type, and perfectly known to one having ordinary skill in the art.

The plate 1 can have several shapes, so that the holes 1a in particular can be aligned or arrayed, all or in part, according to the corners of a triangle or of a quadrilateral. These provisions, in triangle or in quadrilateral, of the screws, improve the stability of its mounting.

It must be noted also that the plate 1, no matter its shape, can be longitudinally bent so as to adapt to the curvature of the bone, consequently enabling the screws 2 to form an angle between them.

The advantages are readily apparent from the description.

The invention claimed is:

1. An implant for compressing together first and second bone parts separated by a joint, the implant comprising:
a plate having a top surface, a bottom bone-contacting surface, and a plurality of holes formed through the top and bottom surfaces, wherein a first of the plurality of holes is arrangeable on a first side of the joint, and a second of the plurality of holes is arrangeable on a second side of the joint, each of the first and second holes being locking holes adapted to receive first and second fixation members, respectively, a central axis of the first hole being directed into the first but not the second bone, and a central axis of the second hole being directed into the second but not the first bone; and
an angled member recessed below the top surface of the plate and extending downward at an angle with respect to the bottom bone-contacting surface, the angled member including a third of the plurality of holes situated between the first and second holes, and a stop surface for engaging with a head of a third fixation member, a central axis of the third hole being angled with respect to a longitudinal axis of the plate, such that when the third fixation member is inserted through the third hole, it is arranged to extend into the first bone, across the joint, and into the second bone, wherein the angled member is situated between and extends below adjacent sides of the plate, such that the angled member is receivable in a cavity formed in at least one of the first and second bones.

2. The implant of claim 1, wherein the angled member is a tab extending from the bottom bone-contacting surface of the plate.

3. The implant of claim 1, wherein the angled member is situated below a guide slot formed in the plate, the guide slot being adapted to allow insertion of the third fixation member through the guide slot and into the third hole.

4. The implant of claim 3, wherein the guide slot is bounded by side walls extending through the top and bottom surfaces of the plate, the side walls being dimensioned to allow insertion of the third fixation member through the guide slot and into the third hole.

5. The implant of claim 1, wherein the central axis of the third hole extends at an angle of between about 30° and 60° with respect to the longitudinal axis of the plate.

6. An implant for compressing together first and second bone parts separated by a joint, the implant comprising:
a plate having a top surface, a bottom bone-contacting surface, and a plurality of holes formed through the top and bottom surfaces, wherein a first of the plurality of holes is arrangeable on a first side of the joint, and a second of the plurality of holes is arrangeable on a second side of the joint, the first and second holes being adapted to receive first and second fixation members, respectively, a central axis of the first hole extending into the first but not the second bone, and a central axis of the second hole extending into the second but not the first bone; and an angled member recessed below the top surface of the plate and extending downward at an angle with respect to the bottom bone-contacting surface, the angled member including a third of the plurality of holes situated between the first and second holes, the third hole being adapted to receive a third fixation member, a central axis of the third hole being angled with respect to a longitudinal axis of the plate, such that when the third fixation member is inserted through the third hole, it is arranged to extend into the first bone, across the joint, and into the second bone, wherein the angled member is situated below a guide slot formed in the plate, the guide slot being adapted to allow insertion of the third fixation member through the guide slot and into the third hole.

7. The implant of claim 6, wherein the first and second holes are locking holes.

8. The implant of claim 7, wherein the first and second holes include threading for engaging with the first and second fixation members.

9. The implant of claim 7, wherein the plate is curved so as to adapt to the curvature of the first and second bones, the curvature of the plate arranging at least two of the fixation members at an angle with respect to one another.

10. The implant of claim 9, wherein at least three of the plurality of holes are arranged according to the corners of a triangle, or at least four of the plurality of holes are arranged according to the corners of a quadrilateral.

11. The implant of claim 6, wherein the angled member is situated between and extends below adjacent sides of the plate, such that the angled member is receivable in a cavity formed in at least one of the first and second bones.

12. The implant of claim 6, wherein the guide slot is bounded by side walls extending through the top and bottom surfaces of the plate, the side walls being dimensioned to allow insertion of the third fixation member through the guide slot and into the third hole.

13. The implant of claim 12, wherein the third hole has a first diameter, and a head of the third fixation member has a second diameter, the second diameter being larger than the first diameter.

14. An implant adapted to span and fuse first and second bone parts, the implant comprising:
a plate having a top surface, a bottom bone-contacting surface, and a plurality of holes formed through the top and bottom surfaces, at least a first and a second of the plurality of holes being situated on a side of the plate corresponding to the first bone part, each of the first and second holes adapted to receive first and second fixation members, respectively; and an angled member recessed below the top surface of the plate and extending downward at an angle with respect to the bottom bone-contacting surface, the angled member including a third of the plurality of holes, the third hole being adapted to receive a third fixation member and being arranged below a guide slot formed in the plate, the guide slot being bounded by side walls extending through the top and bottom surfaces of the plate, wherein the side walls are dimensioned to allow insertion of the third fixation member through the guide slot and into the third hole, and wherein a central axis of the third hole is angled with respect to a longitudinal axis of the plate, such that when the third fixation member is inserted through the third hole, it is arranged to extend from the first bone part and into the second bone part.

15. The implant of claim 14, wherein the angled member includes a stop surface for engaging with a head of the third fixation member, the stop surface acting to prevent over-insertion of the third fixation member through the third hole.

16. The implant of claim 15, wherein the stop surface is situated below the guide slot.

17. The implant of claim 16, wherein a central axis of each of the first and second holes extends into the first bone part but not the second bone part.

18. The implant of claim 17, wherein the angled member is situated between and extends below adjacent sides of the plate, such that the angled member is receivable in a cavity formed in at least one of the first and second bone parts.

19. The implant of claim 14, wherein some of the plurality of holes are arranged according to the corners of a triangle or a quadrilateral.

20. The implant of claim 17, wherein each of the first and second holes are locking holes.

21. The implant of claim 14, wherein the central axis of the third hole diverges from a central axis of at least one of the plurality of holes.

22. The implant of claim 21, wherein the at least one of the plurality of holes is a locking hole.

23. The implant of claim 14, wherein a portion of the implant is insertable in a cavity formed in at least one of the first and second bone parts.

24. The implant of claim 14, wherein the angled member is angled at between about 30° and 60° with respect to the longitudinal axis of the plate.

25. The implant of claim 1, further comprising at least one hole adapted to receive a fixation pin.

26. The implant of claim 1, wherein the plate is curved so as to adapt to the curvature of the first and second bones, the curvature of the plate arranging at least two of the fixation members at an angle with respect to one another.

27. The implant of claim 26, wherein at least three of the plurality of holes are arranged according to the corners of a triangle, or at least four of the plurality of holes are arranged according to the corners of a quadrilateral.

28. The implant of claim 1, wherein the first and second holes include threading for engaging with the first and second fixation members.

29. The implant of claim 6, wherein the angled member is a tab extending from the bottom bone-contacting surface of the plate.

30. The implant of claim 29, wherein the central axis of the third hole extends at an angle of between about 30° and 60° with respect to the longitudinal axis of the plate.

31. A system including the implant of claim 1, in which the system further comprises screws for insertion into the plurality of holes of the implant.

32. The system of claim 31, further comprising a template of the plate for use in determining the positioning of the angled member against bone.

33. The system of claim 32, wherein the template does not include an angled member.

34. A system including the implant of claim 6, in which the system further comprises screws for insertion into the plurality of holes of the implant.

35. The system of claim 34, further comprising a template of the plate for use in determining the positioning of the angled member against bone.

36. The system of claim 35, wherein the template does not include an angled member.

37. A system including the implant of claim 14, in which the system further comprises screws for insertion into the plurality of holes of the implant.

38. The system of claim 37, further comprising a template of the plate for use in determining the positioning of the angled member against bone.

39. The system of claim 38, wherein the template does not include an angled member.

* * * * *